United States Patent [19]

Ranganathan et al.

[11] Patent Number: 5,359,077
[45] Date of Patent: Oct. 25, 1994

[54] PROCESS FOR PREPARATION OF 2-OXO-1 PIPERIDINYL DERIVATIVES

[75] Inventors: Ramachandran S. Ranganathan, Princeton; Thangavel Arunachalam, Plainsboro; Kenneth J. Natalie, Jr, Dayton, all of N.J.

[73] Assignee: Bristol-Myers Squibb Company, Princeton, N.J.

[21] Appl. No.: 893,856

[22] Filed: Jun. 5, 1992

[51] Int. Cl.$^5$ .................. C07D 211/02; C07D 211/40
[52] U.S. Cl. ..................................... 546/219; 546/243
[58] Field of Search ...................... 546/219, 243, 296

[56] References Cited

U.S. PATENT DOCUMENTS 2,333,771 11/1943 Dickey et al. ...................... 260/484
4,734,424 3/1988 Hall et al. ............................ 514/382

FOREIGN PATENT DOCUMENTS 431838 6/1991 European Pat. Off. .
577962 1/1994 European Pat. Off. .

OTHER PUBLICATIONS

March, *Advanced Organic Chemistry*, 3rd ed. A. Wiley-Interscience Publication, (1985), pp. 334–338, 354–355, 364–366, 370–371, 384–385, 388–389.
Guindon et al., *Tetrahedron Letters*, 249) pp. 2969–2972, (1983).
Olah, *Friedel–Crafts and Related Reactions*, vol. IV, Interscience (1965) pp. 31–32.
Wilson, Reactions of Furan Compounds. Part II. Fission of the Tetrahydrofuran and the Tetrahydropyran Ring, J. Chem. Soc., pp. 48–51 (1945).
Goldsmith et al., Cleavage of Cyclic Ethers by Magnesium Bromide–Acetic Anhydride, SN2 Substitution at a Secondary Site, J. Org. Chem., vol. 40, No. 24, pp. 3571–3574 (1975).
Yadav et al., Regioselective Cleavage of 2-Methyltetrahydrofuran: A Versatile Synthesis of 1–Halo–4–pentanols and 4–Halo–1–pentanols, J. Org. Chem., vol. 51, pp. 3372–3374 (1986).
Guindon et al., Regiocontrolled opening of cyclic Ethers using Dimethylboron Bromide, J. Org. Chem., vol. 52, pp. 1680–1686 (1987).
Braun, Organic Syntheses, Coll. Vol. V, 887 (1973).
Stampfli et al., Separation of R(+)- and S(−)-benzyl-3-tetrahydrofuroates using two different Chiral Columns, J. Liquid Chromatography, 13(70, 1285–1290 (1990).
Corina et al., The Mass Spectra of some Benzyl Esters and Thioethers, Organic Mass Spectrometry, vol. 18, No. 2, 60–63 (1983).
Goff et al., "Cleavage of methoxymethyl ethers with boron trichloride. A convenient, versatile preparation of chloromethyl ether derivatives", *J. Org. Chem.*, 51(24), pp. 4711–4714. 1986.
Niwa et al., "A new method for cleavage of aliphata methyl ethers", *Tetrahedron Letters*, 22(42), pp. 4239–4240. 1981.
Kulkarni et al., "Cleavage of cyclic ethers with boron bromide. A convenient route to the bromosubstituted alchols, aldehydes and ketones", *Heterocycles*, 18(Spec. Issue), pp. 163–167. 1982.

*Primary Examiner*—Marianne M. Cintins
*Assistant Examiner*—Phyllis G. Spivack
*Attorney, Agent, or Firm*—Suzanne E. Babajko

[57] ABSTRACT

The process involves ring opening and ring closure of compounds containing a tetrahydrofuroyl group

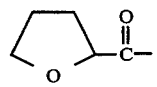

to provide facile synthesis of compounds containing a piperidin-2-one group of the formula

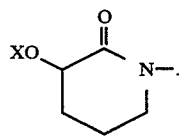

21 Claims, No Drawings

PROCESS FOR PREPARATION OF 2-OXO-1 PIPERIDINYL DERIVATIVES

BRIEF DESCRIPTION OF THE INVENTION

A novel process for preparing compounds of the formula

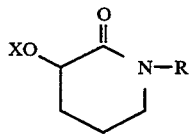   I such as,

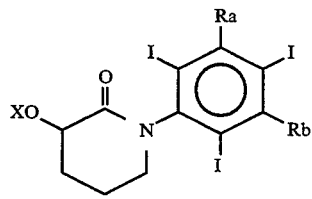   I' is disclosed where X is hydrogen or an oxygen protecting group; R is alkyl, cycloalkyl, aryl, hydroxyalkyl, protected hydroxyalkyl or

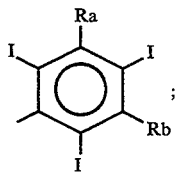 ;

Ra and Rb are independently selected from hydrogen, $-COX_1$,

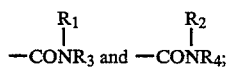

$X_1$ is —OX or a leaving group;

$R_1$ and $R_2$ are the same or different and are hydrogen, alkyl, hydroxyalkyl or protected hydroxyalkyl;

$R_3$ and $R_4$ are the same or different and are hydrogen, alkyl, hydroxyalkyl or protected hydroxyalkyl.

The term alkyl refers to straight or branched chain groups of one to six carbon atoms including methyl, ethyl and propyl.

Hydroxyalkyl refers to such alkyl groups having one or more hydroxy moieties. Preferred hydroxyalkyl groups include

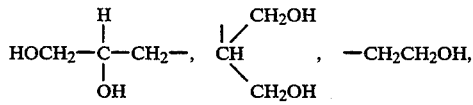

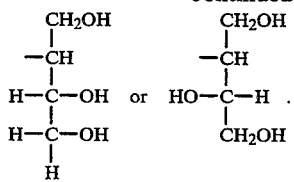

Protected hydroxyalkyl refers to hydroxyalkyl which contains a protecting group instead of hydrogen in the —OH portion. Protected hydroxyalkyl groups include but are not limited to alkoxyalkyl, acyloxyalkyl, 1,3-dioxolanyl or 1,3-dioxanyl.

In a preferred embodiment, the present process comprises treating a compound of the formula

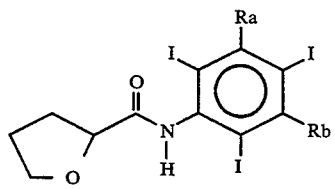   II with a Lewis acid, a source of halide or leaving group and optionally a source of oxygen protection, to provide a compound of the formula

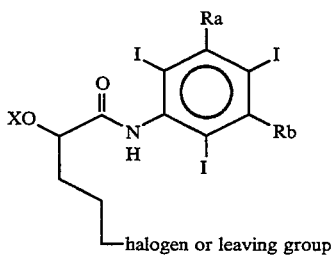   III and thereafter treated with a base to provide the corresponding products of formula I.

DETAILED DESCRIPTION OF THE INVENTION

The present process involves ring opening and ring closure of compounds containing a tetrahydrofuroyl group

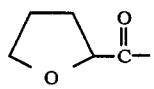

to provide facile synthesis of compounds containing a piperidin-2-one group of the formula

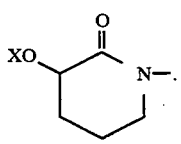

Products, for example, of formula I'

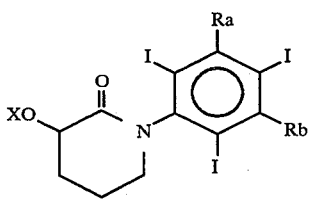

are useful as contrast agents and intermediates therefor. For example, such compounds are disclosed in EP 431,838 and a related copending U.S. application Ser. No. 07/894,681 entitled "Nonionic Radiographic Contrast Agents", (attorney docket RA43c) filed concurrently herewith, which compounds are of the formula

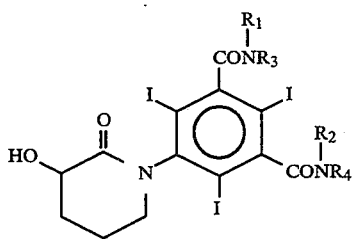

where $R_1$ and $R_2$ are the same or different and are hydrogen or hydroxyalkyl;

$R_3$ and $R_4$ are the same or different and are hydrogen, alkyl or —$CH_2CH_2OH$.

The term alkyl refers to straight or branched chain groups of one to six carbon atoms including methyl, ethyl and propyl.

Hydroxyalkyl refers to such alkyl groups having one or more hydroxy moieties. Preferred hydroxyalkyl groups include

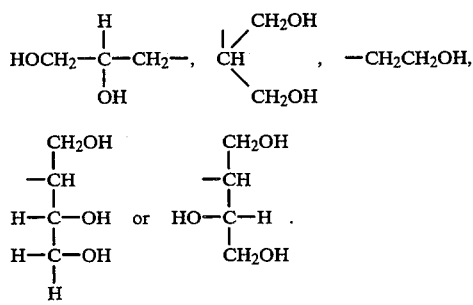

Additional products of formula I, as mentioned above, include intermediates for compounds of Ia such as those having the formula

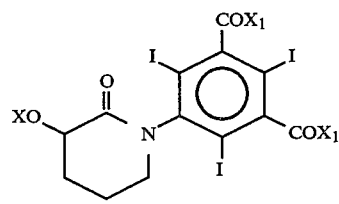

where X is as defined above and $X_1$ is —OX or a leaving group, such as chloro, bromo, and the like.

Compounds of formula Ib are prepared by Scheme A, a preferred embodiment, shown below. Compounds of formula Ia are prepared by Scheme B or by known treatment of intermediates of Ib. Scheme B illustrates that an intermediate containing the tetrahydrofuroyl portion can be ring-opened prior to coupling with the triiodinated phenyl nucleus. Treatment with base to provide ring-closure to a piperidin-2-one group is carried out after coupling to the triiodinated phenyl portion when utilizing Scheme B.

As described above the present process begins with the treatment of tetrahydrofuroyl derivatives, such as inter alia compound II or compound VIII below, with a Lewis acid and a source of halide or leaving group. In a preferred embodiment the Lewis acid can function as the source of halide and use of a separate compound providing additional halide or leaving group is optional. An optional compound can also be added which serves as a source of oxygen protection, X, for the —Ox moiety on the piperidin-2-one products. Further, compounds which serve the dual function of providing a source of halide or leaving group and a source of oxygen protection are also useful herein.

Sources of halide include chlorides, bromides, iodides, carboxylic acid halides, sulfonylhalides, trialkylsilylhalides and the like.

Optional compounds suitable for providing O-protection, but not a halide or leaving group, include anhydrides, e.g., acetic anhydride. Optional compounds suitable for providing a source of halide or leaving group and O-protection for the 3-hydroxy on the piperdinyl moiety include acyl halides, e.g., acetyl chloride, sulfonyl halides, e.g., methanesulfonyl chloride, silyl halides, e.g., trimethylsilyl iodide, mixed (carbonyl-sulfonyl) anhydrides, e.g., acetyl-p-toluene sulfonic anhydride, silyl sulfonates, sulfonic anhydrides and the like.

The term oxygen protecting group is well known in the art and any convenient group can be used. Such known groups, include but are not limited to methyl, benzyl, methoxy-or dimethoxybenzyl, silyl, trialkylsilyl, acyl (e.g., acetyl, formyl), alkylsulfonyl, arylsulfonyl and the like.

The term leaving group refers to groups which form stable anionic species, such as alkylsulfonate, arylsulfonate, halogen, e.g., Cl, Br, I and the like or —OCOalkyl, $ONR_5R_6$ (where $R_5$ and $R_6$ form succinoyl or N-hydroxybenzotriazolyl and the like).

Lewis acids are understood to be any compound capable of accepting an election pair and typical Lewis acids include but are not limited to $BBr_3$, $MgBr_2$, $ZnCl_2$, $(alkyl)_2BBr$, $alkylBBr_2$, $FeCl_3$, $SnCl_4$, $AlCl_3$, $TiCl_3$ and $BF_3$. Preferred Lewis acids are those which also function as a source of halide. Most preferred is $BBr_3$.

Base, as that term is used herein refers to any convenient base and may include sodium bicarbonate, potassium carbonate, sodium hydroxide, potassium t-butoxide, organic bases, e.g., diisopropylamine, triethylamine, pyridine, diazabicyclononane, Hunig's Base and the like.

The present invention is further described in the Schemes below and the explanation which follows, each of which refers to the preferred compounds of I', i.e. where R is Scheme A
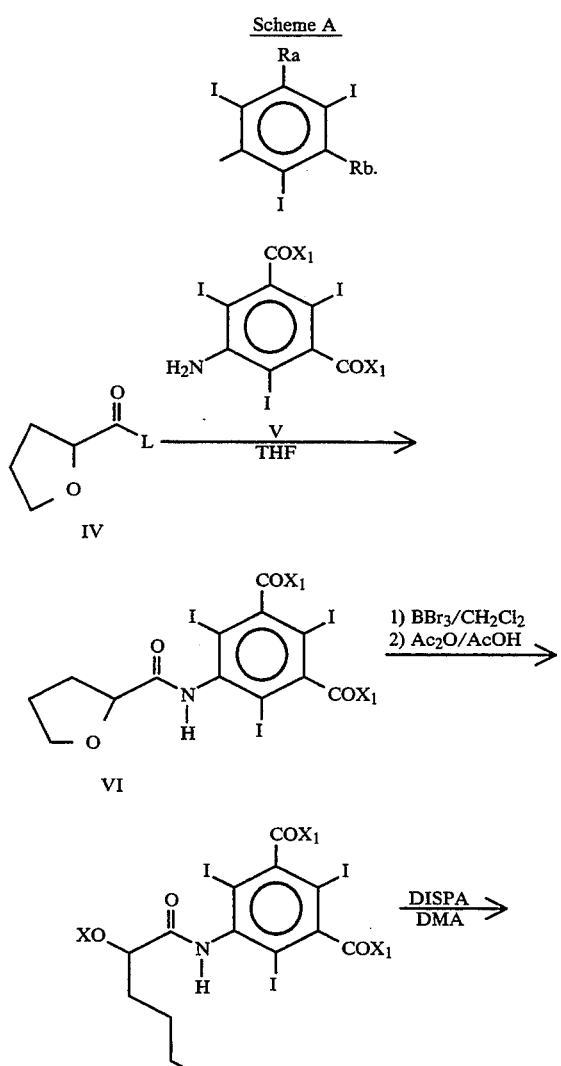
Scheme B
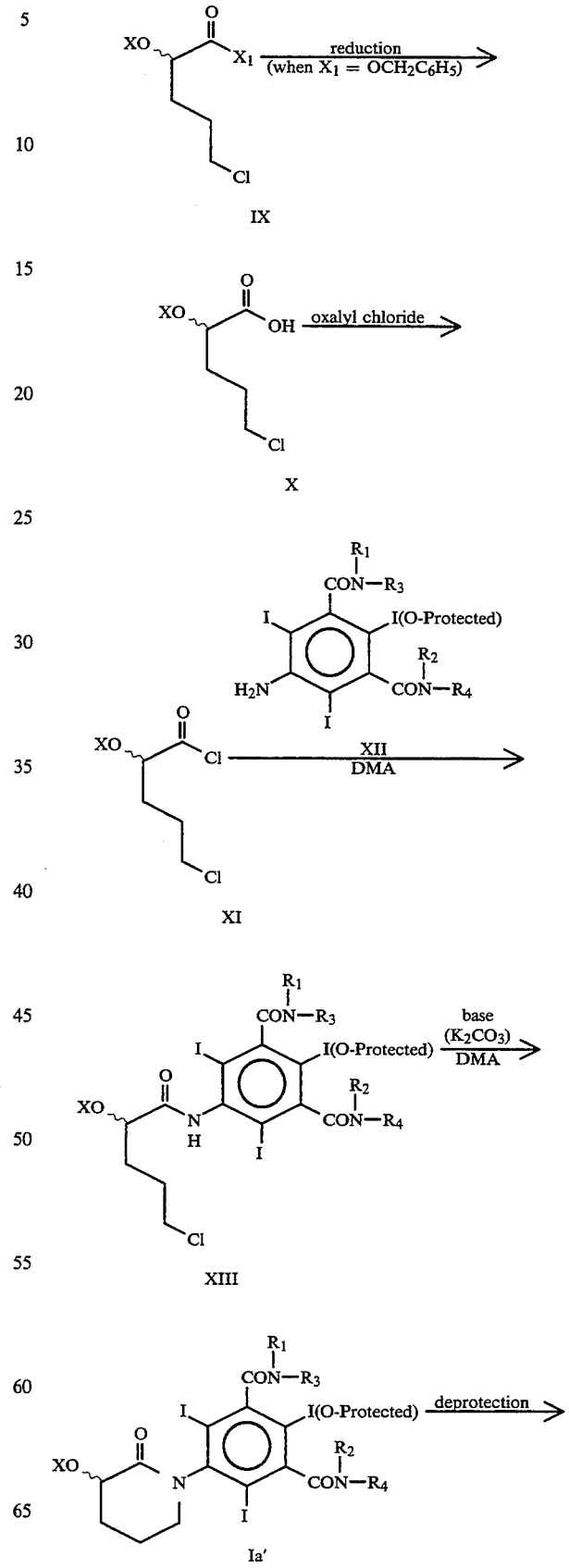

-continued
Scheme B
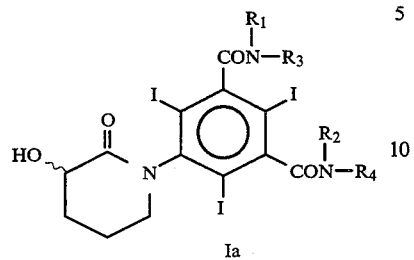
Ia
Scheme C
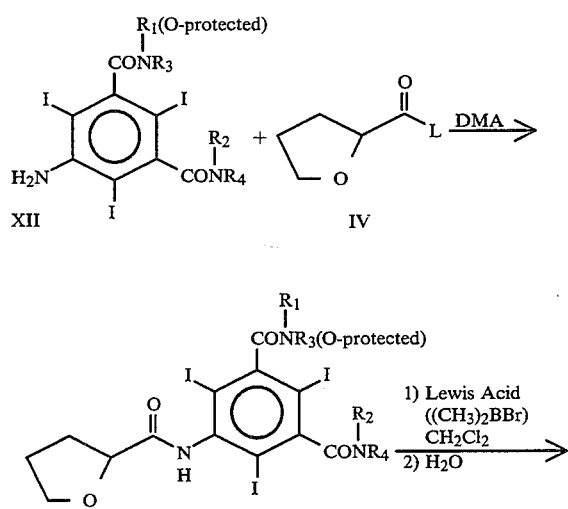
XVI
-continued
Scheme C
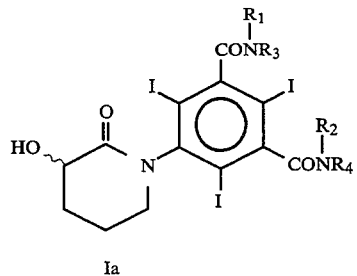
Ia
Scheme D-1
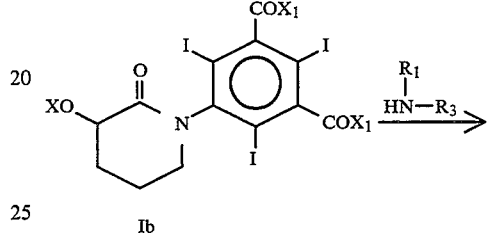
Ib
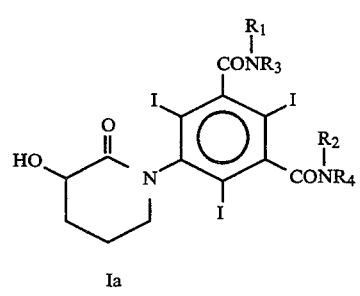
XVII
where $R_1 = R_2$; $R_3 = R_4$
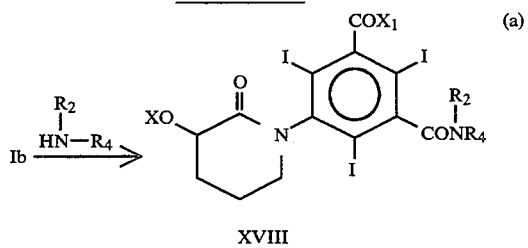
Ia
where $R_1 = R_2$; $R_3 = R_4$
Scheme D-2
(a) Ib $\xrightarrow{\text{HN}(R_2)(R_4)}$ XVIII
(b) XVIII $\xrightarrow{\text{HN}(R_1)(R_3)}$ Ia (where $R_1 \neq R_2$ and/or $R_3 \neq R_4$)

Scheme E

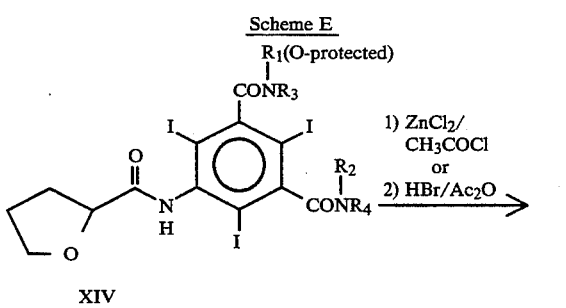

XIV

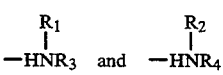

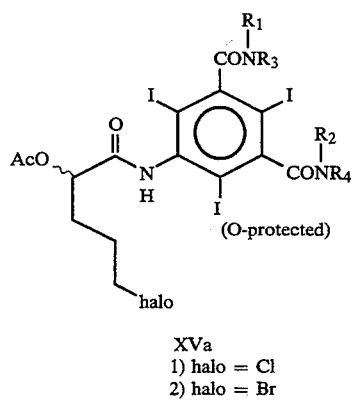

XVa
1) halo = Cl
2) halo = Br

In Scheme A, compound IV, L is a leaving group, e.g., chloro. Accordingly, 2-tetrahydrofuroyl chloride IV is readily prepared by reacting 2-tetrahydrofuroic acid neat, or as a solution in dimethylformamide, with oxalyl chloride under nitrogen, preferably at 25° C. Compound IV is reacted with amine V where $X_1$ is preferably a leaving group, e.g., chloro, in solvents, such as tetrahydrofuran and ethyl acetate, to provide the furancarboxamide VI. Compound VI is treated with a Lewis acid such as $BBr_3$ in $CH_2Cl_2$ followed by further treatment with a source of O-protection, $(X)_2O$, such as acetic anhydride and acetic acid, in the same solvent to provide the ring-opened bromopentanamide VII. Compound VII is then treated with a base, e.g., diisopropylamine, in a solvent, e.g., N,N-dimethylacetamide, preferably under $N_2$ pressure, to provide the ring-closed piperidinyl compound Ib. Conversion of Ib to compounds of Ia is described later in Scheme D.

In Scheme B the tetrahydrofuroyl ring is opened prior to coupling with the triiodinated phenyl group. Accordingly, 2-tetrahydrofuroyl chloride IV is reacted with $HX_1$, such as benzyl alcohol (where $X_1$ is —OX and X is an oxygen protecting group, e.g., benzyl) in a solvent, e.g., pyridine, to provide VIII. Intermediate VIII is thereafter treated with a Lewis acid, e.g., $ZnCl_2$ and XCl (preferably where X is an oxygen protecting group), e.g., acetyl chloride, to provide the chloro-pentanoate intermediate IX. Reductive deprotection of IX by standard methods, e.g., treatment with $H_2$ in the presence of Pd/C, provides compound X which is conveniently activated with, for example, oxalyl chloride to provide the chloro-pentanoyl chloride XI. Reaction of XI with a preferably O-protected-XII, i.e., where hydroxy groups in $R_1-R_4$ are preferably, for example acetyloxy, provides the benzenedicarboxamide XIII. Treatment of XIII with a base, e.g., potassium carbonate, in a solvent, e.g., N,N-dimethylacetamide, affords the pyrrolidin-2-one compound Ia'. Standard deprotection of Ia', for example, via treatment with NaOMe in a solvent, e.g., methanol, provides compounds of Ia.

Scheme C is similar to the approach in Scheme A, that is, the tetrahydrofuroyl-containing compound is coupled to the triiodinated phenyl nucleus prior to ring opening. However, unlike Scheme A, Scheme C utilizes a starting compound XII (preferably O-protected) instead of the bis-acid chloride V, i.e., where the

sidechains are already present. Further, after the Lewis acid $[(CH_3)_2BBr]$ mediated ring opening, the 1,4-bromohydrin XV is directly ring closed to the hydroxy-lactam XVI, without prior protection of the hydroxyl group, in the presence of $K_2CO_3$ in dimethylacetamide.

Schemes D-1 and D-2 convert the Ib products of Scheme A to the products of Ia. When the product of Ia is desired to be a symmetrical amide (i.e., where $R_1=R_2$ and $R_3=R_4$), the products Ib, for example, where $X_1$ is chloro, are reacted with 2.3 equivalents of

in solvents, e.g., acetonitrile and water and in the presence of an organic base, e.g., triethylamine, as shown in Scheme D-1. Where X is other than hydrogen in the products of XVII are deprotected, e.g., with sodium hydroxide to provide the symmetrical amides of Ia.

Scheme D-2 provides unsymmetrical amides of Ia (i.e., where $R_1 \neq R_2$ and/or $R_3 \neq R_4$) by first reacting Ib with 1.1 equivalents of

under conditions as those described in D-1. Intermediate XVIII is thereafter reacted with an excess of

under similar conditions to provide the unsymmetrical amides. Again, as above, if X is other than H, it can be deprotected by known techniques.

For unsymmetrical amides of Ia where one amide is desired to be a primary amide

where $R_1=R_3=H$) and one is to be a secondary or tertiary amide $$\underset{(-NR_4}{\overset{R_2}{|}}$$

where at least one of $R_2$, $R_4 \neq H$), step (a) is preferably carried out first and thereafter the so-formed intermediate XVIII is reacted with ammonia

where $R_1=R_3=H$) to provide the corresponding products of Ia.

Scheme E provides a variation in Scheme C by using the optional compound X—O—halogen (i.e., a source of halide and of O-protection) or $(X)_2O$ (which is also described in Scheme A) along with the Lewis acid in treating compound XIV. The respective compounds used with the Lewis acids in Scheme E are acetyl chloride and acetic anhydride. These directly provide the acetyloxy substituted derivatives of XVa in one step.

In the above reactions, tetrahydrofuroic acid and oxalyl chloride used to prepare compound IV are commercially available. Starting materials V and XII are known and have been described, for example, in EP 431,838. In the above reactions compounds VI, VII, VII, IX, X, XI, XIII and XV, and XVI are novel and are part of the present invention.

The following examples further describe preferred embodiments of the present invention.

EXAMPLE 1

N-[[1,3,4-Trihydroxy-2-butyl]-5-[3-hydroxy-2-oxo-1-piperidinyl]-2,4,6-triiodo-1,3-benzenedicarboxamide A. 2-Tetrahydrofuroyl Chloride 2-Tetrahydrofuroic acid (413.5 mL, 500.0 g) was added to dimethylformamide (1.5 mL) and this was cooled to 15° C. under $N_2$. After purging the reaction vessel with nitrogen for 15 minutes, oxalyl chloride (469.5 mL, 683.1 g) was added dropwise to maintain the temperature at less than 25° C. This required from 3.75 to 5 hours. The crude product was distilled at 65° C. with a vacuum of 2 mm. The reaction mixture was distilled over 40 minutes. An average yield of 548.3 g of the title A product was isolated.

B. N-[3,5-Bis(chlorocarbonyl)-2,4,6-triiodo-phenyl]tetrahydro-2-furancarboxamide N-[3,5-Bis(chlorocarbonyl)-2,4,6-triiodophenyl]amine (230.3 g, 386.6 mmoles) (prepared as described in EP 431,838) was charged to a flask blanketed with nitrogen. Tetrahydrofuran (276 mL, KF <0.03%) was added to the flask and the mixture was agitated at 20° to 25° C. to dissolve the amine. The title A compound (104.0 g, 773.2 mmoles) was added in one portion to the flask. The solution was heated at reflux (65° to 70° C.) under nitrogen for ca. 6 hours until complete. Heptane (552 mL) was added in one portion and the mixture was heated at reflux (ca. 75°–80° C.) for 30 minutes. The suspension was then cooled to 0° to 10° C. over one hour and held at 0° to 10° C. for another hour. The product was by vacuum filtration and washed with 3×350 mL portions of cold (0° to 10° C.) ethyl acetate. Drying the cake at 45° to 50° C. for 10 hours in vacuo (50 mm Hg) afforded 242.3 g of the product.

An 80 g portion of this material was suspended in tetrahydrofuran (640 mL), heated to obtain dissolution, and then filtered. Heptane (1280 mL) was added, the suspension heated at reflux (75 to 78° C.) for 30 minutes, and then cooled to 0° to 10° C. over 90 minutes. After holding the slurry at 0° to 10° C. for another hour, the crystalline product was isolated by vacuum filtration and washed with 3×100 mL portions of cold (0° to 10° C.) ethyl acetate. Drying the cake at 45° to 50° C. for 10 hours in vacuo (50 mm Hg) afforded 71.5 g of high quality title B product (HPLC HI 100).

C. 2-(Acetyloxy)-N-[3,5-bis(chlorocarbonyl)-2,4,6-triiodophenyl]-5-bromopentanamide To a stirred solution of 100 g (0.144 moles) of title B compound in 1L of dry methylene chloride was added 6.80 mL (18.03 g, 0.072 moles) of boron tribromide (99.9%) at room temperature. The resulting slurry was stirred at room temperature. After stirring at room temperature for 2 hours, the reaction was only 92% complete so an additional 0.5 mL of boron tribromide was added. Stirring for another 1 hour resulted in complete conversion to the ring-opened bromo boronate. Then 8.5 mL (0.15 moles) of acetic acid was added followed by 27 mL (0.288 moles) of acetic anhydride and the resulting mixture stirred at reflux (40°–41° C.). The reaction mixture became homogeneous after stirring at reflux for 2 hours. After 4 hours, 500 mL of methylene chloride was removed via distillation, 500 mL of heptane was added and the reaction mixture cooled to room temperature. The resulting white precipitate was collected via filtration and washed with 500 mL of a solution of 50:50 methylene chloride:heptane that had been cooled to 5° C. The resulting white solid was dried under vacuum at 45° C. for 24 hours to yield 98.5 g of the title C product as a white solid, m.p. 194°–195° C.

Analysis calc'd for $C_{15}H_{11}NBrCl_2I_3O_5$: C, 22.06; H, 1.36; N, 1.71; total halogen, 65.07; Found: C, 22.17; H, 1.53; N, 2.04; total halogen, 65.71.

D. 2,4,6-Triiodo-5-[3-(acetyloxy)-2-oxo-1-piperidinyl]-1,3-benzenedicarboxylic acid bis-chloride The title C compound (48.96 g, 60 mM) was dissolved in 100 mL of N,N-dimethylacetamide and the solution was stirred under a positive pressure of nitrogen at 15° C. To this stirred solution diisopropylamine, 7.29 g (72 mM, 10.09 ml) was added in one lot using a syringe under nitrogen. After 30–35 minutes of stirring, an off-white solid started to separate out and the solution became thicker. After 3 hours, the reaction mixture was quenched into cold water (5°–7° C., 1.5 L) containing 12 mL of 1N hydrochloric acid. 10–15 mL of fresh dimethyl-acetamide was used to rinse the reaction flask. The precipitated solids were filtered under suction, the wet cake suspended in 1.5 L of deionized water, stirred for two to three minutes and filtered. The suction dried solids weighed 91.9 g. The material was dried under vacuum at 40°–45° C. overnight yielding 42.4 g of the crude title D compound as an almost colorless crystalline material.

This procedure was repeated to provide an additional 43.0 g of product.

81.29 g of the dried material from the two experiments was combined together and dissolved in 120 mL of dimethylacetamide and filtered under suction. The clear solution was transferred to a three necked round bottomed flask and an additional 20 mL of dimethylacetamide was used for rinsing the filter flask. The solution was stirred and treated with tetrahydrofuran (140 mL) followed by water (125 mL) to a cloud point. The addition of water increased the temperature from 22° to 26° C. The temperature was reduced to 20° C. and kept at 20° for 1 hour and 15 minutes. Thereafter the temperature was brought down to 10° C. and kept at this temperature for 1 hour and 30 minutes. The crystalline solid was filtered and washed with 200 mL of 30% THF/water (V/V) to give 68.57 g of sandy white crystalline powder. This material was dried under vacuum at 40°–45° C. to yield 67.18 g of the title D compound.

E. (5-S-trans) -3-[3-(Acetyloxy)-2-oxo-1-piperidinyl]-5[[(6-hydroxy-2,2-dimethyl-1,3-dioxepan-5-yl)amino]-carbonyl]-2,4,6-triiodo-benzoyl chloride To a solution of the title D compound (6.6 g, 9 mmol) in anhydrous dimethyacetamide (40 ml) was added triethyl amine (0.9 g, 9 mmol) and 4-amino-5-hydroxy-2,2-dimethyl-1,3-dioxepane (1.6, 9.9 mmol) and the mixture was stirred at room temperature for 16 hours. Dimethylacetamide was removed in vacuo and the residue was dissolved in ethyl acetate (150 ml), washed with water (100 ml), dried and solvent removal afforded the crude mono amide. The crude material was purified by column chromatography over silica gel (300 g) using hexane/ethyl acetate as the eluent to afford pure title E mono-amide-mono-acid chloride (5.3 g) as a colorless glassy solid.

Elemental analysis calc'd for $C_{22}H_{24}N_2O_8I_3Cl$: C, 30.70, H, 2.81; N, 3.26; Cl, 4.12; I, 44.24; Found: C, 30.89; H, 2.73; N, 3.26; Cl, 4.08; I, 43.86.

F. N-[[1,3,4-Trihydroxy-2-butyl]-5-[3-hydroxy-2-oxo-1-piperidinyl]-2,4,6-triiodo-1,3-benzene-dicarboxamide A solution of the title E compound (4.4 g, 5.1 mmol) in anhydrous dimethylacetamide (20 ml) was cooled and treated in a steel bomb with anhydrous ammonia (4 ml) at −78° C. The temperature of the reaction mixture was allowed to rise slowly to room temperature and the mixture was stirred for 18 hours. Ammonia was allowed to evaporate off and the resulting product without isolation was treated with 5M sodium hydroxide solution (2.0 ml) for 2 hours. At the end of 2 hours, the pH of the reaction mixture was adjusted to 0.5 with concentrated hydrochloric acid and the mixture stirred for 16 hours. The solvents were removed in vacuo and the residue dissolved in water (400 ml), the pH adjusted to 7 and the solution loaded on to a CHP-20P column (500 ml). The column was initially eluted with water to remove all the salts and then with water containing increasing amounts of ethanol. The product was eluted with 7–8% ethanol. Fractions containing the pure product were combined and solvent removal afforded pure title product as a colorless glassy solid (3.42 g, yield 88%).

Elemental analysis calc'd for $C_{22}H_{24}N_2O_8I_3Cl$: C, 26.90, H, 2.66; N, 5.54; I, 50.15; Found: C, 26.96; H, 2.81; N, 5.38; I, 50.54.

EXAMPLE 2

N,N'-bis(2,3-Dihydroxypropyl)-5-(3-hydroxy-2-oxo-1-piperidinyl)-2,4,6-triiodo-1,3-benzenedicarboxamide A. N,N'-bis(2,3-Dihydroxypropyl)-5-(3-acetyloxy-2-oxo-1-piperidinyl)-2,4,6-triiodo-1,3-benzenedicarboxamide To 50 g of the title D compound of Example 1 was added 544 mL of acetonitrile and 21.8 mL of triethylamine. A good agitation was maintained all through the reaction. (±)3-Amino-1,2-propanediol (APD), 14.24 g, dissolved in 68 mL of deionized water was then added within 10 minutes. Another 68 mL of deionized water was used to rinse the flask, in which the APD solution was made, and the addition funnel. The rinsings were also added to the reaction mixture. An endotherm of 7°–10° C. was observed. After the additions were complete, the reaction mixture was maintained at 25°–28° C. The reaction mixture which was initially a suspension became a clear solution after about 2 to 3 hours from the commencement of the addition of APD. Progress of the reaction was monitored by an in-process HPLC assay.

As the reaction progressed, the bis coupled product maximized in about 10 hours. At the end of this time, the reaction flask was equipped for vacuum distillation and the solvent was removed under reduced pressure (approximately 30 inches of mercury) to obtain a final volume of 160 mL of a pale yellow colored solution (pH=8.65). This solution was used in the next step for purification on ion-exchange resins.

The so-prepared reaction mixture was allowed to drip on a resin bed and the elution rate was maintained at 25–30 mL/min. After the solution had been passed through the resin, the separatory funnel was charged with deionized water and elution was continued. Seventeen fractions, 250 mL each in volume, were collected. After assaying all the fractions by HPLC, fractions 1–8 were combined to obtain a total volume of 1750 mL (pH=4.4). This solution containing the title A product was used in the hydrolysis step.

B. N,N'-bis(2,3-Dihydroxypropyl)-5-(3-hydroxy-2-oxo-1-piperidinyl)-2,4,6-triiodo-1,3-benzene-dicarboxamide To the solution containing the title A compound (1750 mL) obtained in the previous step was added 86 mL of IRA 900C (OH—) resin (1.7 equiv) and the suspension was agitated at 50°–55° C. Progress of the hydrolysis was monitored by an in-process HPLC assay. After about 5 hours, 29 mL more of the resin was added and the reaction was continued for an additional 2 hours. At the end of this time, the solution was brought to room temperature and filtered on a medium porosity sintered glass funnel. After disconnecting the vacuum, approximately 200 mL of deionized water was passed through the resin under gravity. The original filtrate and the water wash were combined to obtain a total volume of 2160 mL.

2-Butanol (230 mL) was heated and maintained at 38°–40° C. The solution from above was concentrated to dryness on a rotary evaporator keeping the bath temperature at 45°–50° C. to obtain 47.5 g of a solid. Of this, 43.4 g was dissolved in 76.5 mL of methanol and filtered. The clear filtrate was transferred to the addition funnel and added dropwise over a period of 25–30 minutes to the 2-butanol. An immediate precipitation of product took place. After the addition, the slurry was stirred for an additional hour at the same temperature and then cooled to 0° C. for 30 minutes. The resulting solid was then filtered and dried in a vacuum oven at 46° C. for 16 hours to obtain 38.3 g of crude solid.

A 1-L three necked flask fitted with a mechanical stirrer and an addition funnel was charged with 375 mL of acetone. The above solid material (37.5 g), dissolved in 75 mL of methanol, was transferred to an addition funnel and then added dropwise to 375 mL of acetone kept at 40° C. over a period of 20 minutes. An immediate precipitation of product took place. After the addition, the slurry was cooled to 0° C. over a period of 30 minutes and held at the same temperature for an additional 30 minutes. The solid obtained was filtered, washed with 25 mL of acetone and dried in a vacuum oven at 45° C. for 16 hours to obtain 32.7 g of a white solid. The material isolated (21 g) was dissolved in 100 mL of deionized water and the solution obtained was concentrated to dryness under reduced pressure (20 mm of Hg) keeping the bath temperature at approximately 45° C. Final drying of the material was achieved in a vacuum oven at 60° C. for 16 hours to obtain 18 g of the title B product as a glassy solid.

EXAMPLE 3

Alternate synthesis for compound of Example 2

N, N'-Bis(2,3-Dihydroxypropyl) -5-(3-hydroxy-2-one-1-piperidinyl)-2,4,6-triiodo-1,3-benzenedicarboxamide A. Tetrahydrofuroyl chloride Oxalyl chloride (63.5 g, 500 mmol) was added dropwise to tetrahydrofuroic acid 23.2 g, 200 mmol) at 0°. The solution was then stirred overnight at room temperature. Removal of excess oxalyl chloride (60°, 20 mm Hg), followed by distillation of the residue provided the desired tetrahydrofuroyl chloride as a colorless liquid (23.8 g), b.p. 88°–92° at 20 mm Hg.

B. Benzyl tetrahydrofuroate

Tetrahydrofuroyl chloride (15.0 g, 112 mmol) was added dropwise to a cold solution of benzyl alcohol (10.9 g, 101 mmol) and pyridine (20.0 g, 253 mmol) in $Et_2O$ (200 mL). The solution was stirred at 0° for 40 minutes, then filtered to remove the side product pyridine hydrochloride. The filtrate was washed with 0.1M HCl (50 mL), saturated aqueous $NaHCO_3$ (50 mL), and brine (50 mL), and then dried over $MgSO_4$. Filtration and evaporation of the solvent gave a yellow oil, which was distilled. Benzyl tetrahydrofuroate was obtained as a colorless oil (21.1 g), b.p. 118° to 120° at 0.5 mm Hg. Microanalysis calc'd for $C_{12}H_{14}O_3$(206.2): C, 69.89; H, 6.84; O, 23.27; Found: C, 69.62; H, 6.89.

C. Benzyl 2-acetyloxy-5-chloro-pentanoate

To a suspension of freshly fused $ZnCl_2$ (35 mg, 0.25 mmol) in acetyl chloride (31 mL, 436 mmol) was added dropwise benzyl tetrahydrofuroate (15 g, 72 mmol). The mixture was heated at reflux for 17 hours, by which time it turned black. Excess $CH_3COCl$ was evaporated and the residue dissolved in $Et_2O$ (200 mL). This solution was washed twice with saturated aqueous $NaHCO_3$ (50 mL). The organic layer was dried over $MgSO_4$, filtered and evaporated. The black residue was chromatographed over silica gel, eluting with 20:80 EtOAc-heptane. Fractions containing the desired ester were combined and evaporated to give a yellow oil. This oil was distilled to give the title C compound as a faintly yellow oil, which crystallized after several days in the refrigerator (17.6 g), b.p. 144 to 152° at 0.1 mm Hg, m.p. 40 to 41°.

Microanalysis calc'd for $C_{14}H_{17}O_4Cl$ (284.7): C, 59.06; H, 6.02; Cl, 12.45; O, 22.48; Found: C, 59.22; H, 6.04; Cl, 12.63:

D. 2-Acetyloxy-5-chloro-pentanoic acid

5% Palladium on carbon (0.96 g) was suspended in a solution of the title C compound (15.3 g, 53.7 mmol) in ethyl acetate (170 mL) and HOAc (9.0 mL). The solution was shaken under an atmosphere of hydrogen (10 psi) for 1 hour, then filtered through a bed of celite. The solvent was evaporated and the residual oil was distilled to give the title D compound as a colorless oil (9.1 g), b.p. 135° to 136° at 0.03 mm Hg.

Microanalysis calc'd for $C_7H_{11}O_4Cl$ (194.6): C, 43.20; H, 5.70; Cl, 18.22; O, 32.88; Found: C, 42.95; H, 5.80; Cl, 17.84.

E. 2-Acetyloxy-5-chloro-pentanoyl chloride

Oxalyl chloride (13.1 g, 103 mmol) was added to the title D compound (7.99 g, 41.1 mmol) and stirred at 25° overnight. Distillation gave unreacted oxallyl chloride followed by the title E compound (8.51 g), b.p. 76°–78° at 0.5 mm Hg).

F. N,N-Bis[2,3-bis(acetyloxy)propyl]-5-[(2-acetyloxy-5-chloro-1-oxopentyl)-amino]-2,4,6-triiodo-1,3-benzenedicarboxamide The title E compound (2.77 g, 13.0 mmol) was added dropwise to a cold solution of N,N'-bis[2,3-bis (acetyloxy)propyl]-5-amino-2,4, 6-triiodo-1,3-benzenedicarboxamide (prepared as described in EP 431,838) (8.73 g, 10.0 mmol) in dry DMA (400 mL). The solution was stirred at 25° overnight. The reaction mixture was purged with $N_2$ for 30 minutes to remove as much HCl as possible, then dissolved in EtOAc (200 mL) and washed with $H_2O$ (100 mL), cold saturated aqueous $NaHCO_3$ (50 mL), and brine (50 mL). The organic layer was dried over $MgSO_4$, filtered, and evaporated to obtain a yellow foamy solid. This solid was chromatographed over silica gel and eluted with 70:30 EtOAc-heptane. Fractions containing the product were combined and evaporated to give the title F compound as a white foamy solid (8.31 g). TLC: Rf 0.48 on silica gel, EtOAc, UV.

G. N,N-Bis[2,3-bis(acetyloxy)propyl]-5-(3-acetyloxy-2-oxo-1-piperdinyl)-2,4,6-triiodo-1,3-benzenedicarboxamide Powdered $K_2CO_3$ (3.32 g, 24 mmol) was added to a solution of the title F compound (6.00 g, 57.1 mmol) in DMA (29 mL) and stirred at 25° overnight. The reaction mixture was filtered and evaporated. The residual yellow oil was dissolved in ethyl acetate (100 mL) and washed with $H_2O$ (50 mL) and brine (50 mL). The organic layer was dried over $MgSO_4$, filtered, and evaporated to give a white foamy solid. This solid was chromatographed over silica gel and eluted with 80:20 ethyl acetate-heptane. Fractions containing the pure product were combined and evaporated to give the title G compound as a white foamy solid (4.56 g). This product was identified in all respects with the pentaacetate previously described in EP431,838 and in RA43c.

H. N,N'-Bis(2,3-Dihydroxypropyl)-5-(3-hydroxy-2-one-1-piperidyl)-2,4,6-triiodo-1,3-benzene-dicarboxamide To a solution of the title G compound (25 mg, 0.026 mmol) in anhydrous methanol (3 mL) was added a solution of sodium methoxide in methanol (0.2 mL/0.5M solution), and the mixture stirred for 2 hours. The solution was neutralized by addition of AG 50 W-X8($H^+$) resin which was filtered off and the filtrate concentrated to give 17 mg of the title product. This product was identical in all respects with the product of Title B, Example 2.

EXAMPLE 4

5-[3-(Acetyloxy)-2-oxo-1-piperdinyl]-N,N-bis[2,3-bis-(acetyloxy)propyl]-2,4,6-triiodo-1,3-benzene-dicarboxamide A. N,N'-Bis[2,3-bis(acetyloxy)propyl]-2,4,6-tri-iodo-5-[[(tetrahydro-2-furanyl)carbonyl]-amino]-1,3-benzenedicarboxamide To a stirred solution of N,N'-bis[2,3-bis (acetyloxy)-propyl]-5-amino-2,4,6-triiodo-1,3-benzenedicarboxamide (8.73 g, 10 mmol) (prepared as described in EP 431,838) in N,N-dimethylacetamide (30 mL), was added in drops tetrahydrofuran-2-carbonyl chloride (1.8 g, 13 mmol) (prepared as in part A of Example 3) at 0°–5°. After the addition, the mixture was stirred at 0°–5° for 0.5 hour, then at room temperature for 20 hours. Nitrogen gas was purged through the solution for 0.25 hour, and the N,N-dimethylacetamide was removed in vacuo at 40°. The residue was dissolved in ethyl acetate (200 mL), and the solution was washed successively with cold aqueous sodium bicarbonate (2×50 mL), water (2×50 mL) and saturated sodium chloride (2×50 mL). After drying over sodium sulfate, the solvent was removed in vacuo to obtain the title B furanilide as an off-white foamy material (9.27 g, crude). The crude product (7.2 g), upon purification by column chromatography over silica gel (mobile phase: hexane/ethyl acetate) furnished N,N'-bis[2,3-bis(acetyloxy)propyl]2,4,6-triiodo-5-[[(tetrahydro-2furanyl)carbonyl]amino]-1,3-benzenedicarboxamide (6.19 g), m.p. 101°–104°.

Elemental analysis calc'd for $C_{27}H_{32}I_3N_3O_{12}$ (971.28): C, 33.39; H, 3.32; I, 39.20; N, 4.33; O, 19.77; Found: C, 33.39; H, 3.27; I, 38.78; N, 4.26.

B. 5-[3-(Acetyloxy)-2-oxo-1-piperdinyl]-N,N-bis-[2,3-bis(acetyloxy)propyl]-2,4,6-triiodo-1,3-benzenedicarboxamide.

To a stirred solution of the title A furanilide (194 mg, 0.2 mmol) in dry ethyl acetate (5 mL) was added the HBr—Ac₂O reagent (3 mL, prepared by passing HBr gas through acetic anhydride at 0°–5° for 2 hours) at 0°–5°. The mixture was stirred at 5° for 2 hours, and then at room temperature for 75 hours. Nitrogen gas was purged through the reaction mixture for 15 minutes, and the solvent was evaporated in vacuo at 40°. The residue was dissolved in ethyl acetate (50 mL), and the solution washed successively with water, cold aqueous saturated $NaHCO_3$, water and brine. After drying over $Na_2SO_4$, the solvent was removed in vacuo to obtain the alpha-acetyloxy-omega-bromopentanoylanilide as a brownish semi-solid (220 mg). This material was immediately subjected to intramolecular cyclization by stirring with powdered potassium carbonate (0.3 g) in N,N-dimethylacetamide (5 mL) overnight. The mixture was filtered, and the solid material washed with ethyl acetate (20 mL). The filtrate was concentrated in vacuo to yield a brownish semi-solid, which, upon purification by silica gel chromatography using hexane/ethyl acetate, furnished the desired penta-acetate (99 mg) as a white amorphous solid. This product was identical in all respects with the product of Title G, Example 3.

The corresponding piperidinyl products were prepared using the methodology in Examples 1–3.

EXAMPLE 5

5-[3-(Acetyloxy)-2-oxo-1-piperdinyl]-N,N-bis[2,3-bis (acetyloxy)propyl]-2,4,6-triiodo-1,3-benzenedicarboxamide To a stirred solution of the title A furanilide of Example 4 (194 mg, 0.2 mmol) in dry ethyl acetate (5 mL) was added freshly fused and powdered $ZnCl_2$ (6 mg). The mixture was placed in a preheated oil-bath (80°–85°) and stirred for 5 minutes when a homogeneous solution was obtained. To this was added acetyl chloride (0.4 mL) dropwise, and the mixture stirred at 80°–85° for 12 hours. The solvents were removed in vacuo, and the residue partitioned between ethyl acetate (50 mL) and water (10 mL). The organic layer was washed with water, dried over $Na_2SO_4$, and the solvent removed in vacuo to yield the alpha-acetyloxy-omega-chloro-pentanoylanilide as a dark gummy residue (210 mg). This was dissolved in N,N-dimethylacetamide (5 mL), treated with powdered potassium carbonate (0.2 g) and the mixture stirred overnight. The solid material was filtered off, and the filtrate concentrated in vacuo to give a brownish gummy product. Purification of this material by preparative TLC ($CHCl_3$/ MeOH 9:1) furnished the penta-acetate as a white amorphous solid (61 mg). This product was identical in all respects with the product of Title G, Example 3.

The corresponding deprotected piperidinyl product was prepared using the methodology in Examples 1–3.

EXAMPLE 6

N,N'-Bis[2,3-bis(acetyloxy)propyl]-5-(3-hydroxy-2-oxo-1-piperidinyl)-2,4,6-triiodo-1,3-benzenedicarboxamide To a stirred solution of N,N'-bis[2,3bis (acetyloxy)propyl]-2,4,6-triiodo-5-[[(tetrahydro-2-furanyl)carbonyl]amino]-1,3-benzenedicarboxamide (0.25 g, 0.26 mmol) (the title compound of Example 4) in dry $CH_2Cl_2$ (5 mL) was added triethyl amine (0.01 mL). The solution was cooled to 0°–5°, and to this was added dropwise a solution of dimethylboron bromide in $CH_2Cl_2$ (0.12 g, 0.5 mL/2 mMol solution in $CH_2Cl_2$). After stirring the mixture at 0°–5° for 6–8 hours, the mixture was added to a vigorously stirred solution of aqueous saturated sodium bicarbonate (5 mL). After stirring for 5 minutes, ethyl acetate (50 mL) and water (10 mL) were added. The organic layer was separated, washed with water, dried over anhydrous sodium sulfate, and concentrated in vacuo to yield the omega-bromo-alpha-hydroxypentanoyl anilide as an off-white fluffy solid (260 mg).

The material was immediately subjected to intramolecular cyclization by stirring a mixture of the anilide (260 mg) and powdered potassium carbonate (250 mg) in N,N-dimethylacetamide (5 mL) for 15 hours. The mixture was filtered, and the cake washed with ethyl acetate. The combined filtrate was concentrated in vacuo to yield a brownish solid (230 mg), which upon purification by silica gel chromatography (hexane/ethyl acetate) furnished pure N,N'-bis[2,3-bis-(acetyloxy)propyl]-5-(3-hydroxy-2-oxo-1- piperidinyl)-2,4,6-triiodo-1,3-benzenedicarboxamide as a white fluffy solid (134 mg).

Elemental analysis calc'd for $C_{27}H_{32}I_3N_3O_{12}$ (971.28)+0.78 $H_2O$: C, 32.92; H, 3.43; I, 28.64; N, 4.26; O, 20.75; Found: C, 33.24; ; H, 3.13; I, 38.34; N, 3.94; $H_2O$, 1.42.

The corresponding deprotected piperidinyl product was prepared using the methodology in Examples 1–3.

What is claimed is:

1. A process for preparing a compound of the formula

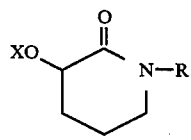

where X is hydrogen or an oxygen protecting group;
R is alkyl, cycloalkyl, aryl, hydroxyalkyl, protected hydroxyalkyl or

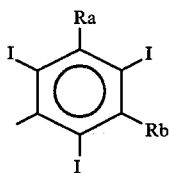

Ra and Rb are independently selected from hydrogen, —COX$_1$,

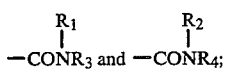

X$_1$ is —OX or a leaving group;
R$_1$ and R$_2$ are the same or different and are hydrogen, alkyl, hydroxyalkyl or protected hydroxyalkyl;
R$_3$ and R$_4$ are the same or different and are hydrogen, alkyl, hydroxyalkyl or protected hydroxyalkyl;
the term alkyl refers to straight or branched chain groups of one to six carbon atoms;
hydroxyalkyl refers to said alkyl groups having one or more hydroxy moieties;
which process comprises treating a compound of the formula

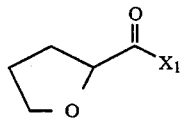
VIII where in said formula VIII, X$_1$ is —OX and X is an oxygen protecting group; with a Lewis acid, a source of halide or leaving group and, optionally, a source of oxygen protection selected from anhydrides; sulfonyl halides; silyl halides; mixed anhydrides; silyl sulfonates; sulfonic anhydrides; and acyl halides for the protection of the oxygen of the group XO of the following compound of formula IX, said oxygen present as a member of the tetrahydrofuran ring of formula VIII, to provide a compound of formula IX

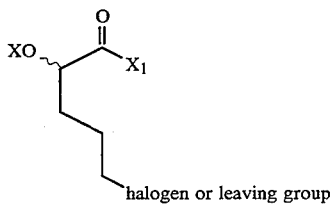
IX reducing the compound IX to provide

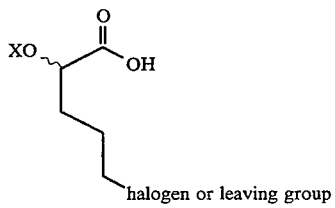
X activating compound X to provide

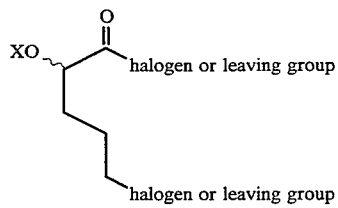
XI reacting compound XI with a compound of the formula

H$_2$NR to provide

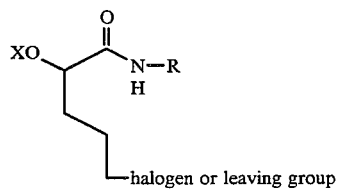

and thereafter treating the so-formed compound with a base;
wherein said leaving group is
halogen,
alkylsulfonate,
arylsulfonate,
—OCOalkyl,
ONR$_5$R$_6$ where R$_5$ and R$_6$ together with the N to which they are attached form succinoyl or N-hydroxybenzotriazoyl; or
a group derived from carboxylic acid halides, sulfonyl halides, trialkylsilylhalides; or said Lewis acid, when said Lewis acid is also a source of halide; or optionally, said source of oxygen protection, when said source of oxygen protection also functions as a source of halide or leaving group.

2. The process of claim 1 wherein R is

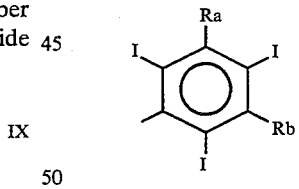

3. The process of claim 1 wherein said Lewis acid is also said source of halide.

4. The process of claim 3 wherein said Lewis acid is selected from BBr$_3$, ZnCl$_2$, (alkyl)$_2$—BBr, alkyl-BBr$_2$, FeCl$_3$, SnCl$_4$, AlCl$_3$, TiCl$_3$, and MgBr$_2$.

5. The process of claim 4 wherein said Lewis acid is BBr$_3$ or (CH$_3$)$_2$BBr.

6. The process of claim 1 wherein said source of halide or leaving group is selected from carboxylic acid halides, sulfonyl halides and trialkylsilylhalides.

7. The process of claim 6 wherein said source of halide or leaving group is acetyl chloride, trimethylsilyliodide, or p-toluenesulfonyl chloride.

8. The process of claim 1 wherein said optional source of oxygen protection is selected from anhydrides, sulfonyl halides, silyl halides, mixed anhydrides, silyl sulfonates and sulfonic anhydrides.

9. The process of claim 1 wherein said source of oxygen protection also functions as said source of halide or leaving group and is selected from acyl halides, sulfonyl halides, silyl halides, mixed anhydrides, silyl sulfonates and sulfonic anhydrides.

10. The process of claim 8 wherein said source of oxygen protection is acetic anhydride.

11. The process of claim 9 wherein said source of oxygen protection and source of halide are selected from acetyl chloride, methanesulfonyl chloride, trimethylsilyl iodide and acetyl-p-toluene sulfonic anhydride.

12. The process of claim 1 wherein said oxygen protecting group, X, is selected from methyl, benzyl, methoxybenzyl, dimethoxybenzyl, silyl, trialkylsilyl, acyl, alkylsulfonyl and arylsulfonyl.

13. The process of claim 12 wherein said oxygen protecting group is selected from benzyl and acyl.

14. The process of claim 13 wherein said oxygen protecting group is acetyl.

15. The process of claim 1 wherein said leaving groups are selected from halogen, alkylsulfonate, arylsulfonate, —OCOalkyl and $ONR_5R_6$ where $R_5$ and $R_6$ together with the N to which they are attached form succinoyl or N-hydroxybenzotriazoyl.

16. The process of claim 15 wherein said leaving group is selected from halogen being Cl, Br or I.

17. The process of claim 1 wherein said base is selected from sodium bicarbonate, potassium carbonate, sodium hydroxide, potassium t-butoxide, diisopropylamine, triethylamine, pyridine, diazabicyclononane and Hunig's base.

18. The process of claim 17 wherein said base is selected from potassium carbonate, sodium bicarbonate and diisopropylamine.

19. The process of claim 1 wherein compound VIII is treated with a Lewis acid and an acyl halide, and further where throughout the process X is acetyl, $X_1$ is chloro, Ra is $$-NR_3\overset{R_1}{\underset{|}{}}$$

and Rb is $$-NR_4\overset{R_2}{\underset{|}{}}.$$

20. The process of claim 19 wherein said Lewis acid is $ZnCl_2$ and said acyl halide is acetyl chloride.

21. The process of claim 1 wherein said compound of formula I is selected from

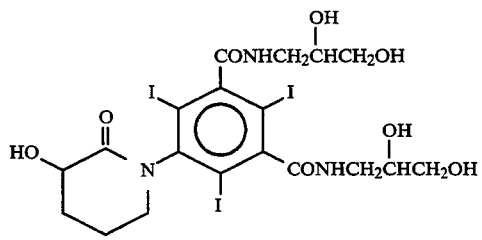

and

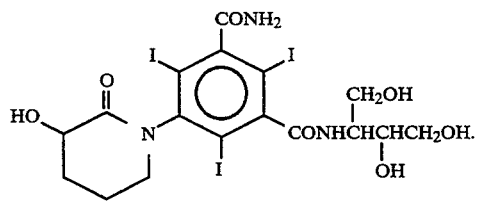

* * * * *